United States Patent [19]

Kaiser

[11] Patent Number: 5,891,061
[45] Date of Patent: Apr. 6, 1999

[54] BRACE FOR APPLYING A DYNAMIC FORCE TO A JOINTED LIMB

[75] Inventor: Robert T. Kaiser, Southampton, N.J.

[73] Assignee: Jace Systems, Inc., Mount Laurel, N.J.

[21] Appl. No.: 803,110

[22] Filed: Feb. 20, 1997

[51] Int. Cl.$^6$ .................................................. A61F 5/00
[52] U.S. Cl. ................... 601/33; 602/16; 602/20
[58] Field of Search ................... 602/5, 16, 20, 602/23, 26; 601/23, 33

[56] References Cited

U.S. PATENT DOCUMENTS

| | | |
|---|---|---|
| Re. 32,650 | 4/1988 | Waddell . |
| 183,376 | 10/1876 | Darrach . |
| 2,387,966 | 10/1945 | Zander . |
| 2,632,440 | 3/1953 | Hauser et al. . |
| 2,646,793 | 7/1953 | Swiech et al. . |
| 3,717,144 | 2/1973 | Bimler . |
| 3,928,872 | 12/1975 | Johnson . |
| 3,958,569 | 5/1976 | Vosburgh . |
| 4,100,918 | 7/1978 | Glancy . |
| 4,214,577 | 7/1980 | Hoy . |
| 4,252,111 | 2/1981 | Chao et al. . |
| 4,340,041 | 7/1982 | Frank . |
| 4,361,142 | 11/1982 | Lewis et al. . |
| 4,370,977 | 2/1983 | Mauldin et al. . |
| 4,456,003 | 6/1984 | Allard et al. . |
| 4,508,111 | 4/1985 | Hepburn . |
| 4,556,053 | 12/1985 | Irons . |
| 4,602,627 | 7/1986 | Vito et al. . |
| 4,612,919 | 9/1986 | Best . |
| 4,614,181 | 9/1986 | Karlsson . |
| 4,688,559 | 8/1987 | Vito et al. . |
| 4,777,941 | 10/1988 | Borig et al. . |
| 4,781,180 | 11/1988 | Solomonow . |
| 4,838,251 | 6/1989 | Chignon et al. . |
| 4,846,842 | 7/1989 | Connolly et al. . |
| 4,848,326 | 7/1989 | Lonardo . |
| 4,865,024 | 9/1989 | Hensley et al. . |
| 4,871,588 | 10/1989 | Cuddy et al. . |
| 4,905,678 | 3/1990 | Cumins et al. . |
| 4,928,676 | 5/1990 | Pansiera . |
| 4,958,643 | 9/1990 | Paniera . |
| 4,982,732 | 1/1991 | Morris . |
| 4,986,264 | 1/1991 | Miller . |
| 5,000,169 | 3/1991 | Swicegood et al. . |
| 5,002,044 | 3/1991 | Carter . |
| 5,013,037 | 5/1991 | Stermer . |
| 5,036,837 | 8/1991 | Mitchell et al. . |
| 5,103,811 | 4/1992 | Crupi, Jr. . |
| 5,117,814 | 6/1992 | Luttrell et al. ............................ 601/33 |
| 5,167,612 | 12/1992 | Bonutti ................................ 601/33 X |
| 5,213,094 | 5/1993 | Bonutti ..................................... 601/33 |
| 5,219,323 | 6/1993 | Singer et al. ........................ 601/33 X |
| 5,395,303 | 3/1995 | Bonutti et al. ........................ 601/33 X |
| 5,453,075 | 9/1995 | Bonutti et al. ........................ 601/33 X |
| 5,456,268 | 10/1995 | Bonutti ................................ 601/33 X |
| 5,472,410 | 12/1995 | Hammersly ........................... 601/33 X |
| 5,686,830 | 11/1997 | Bonutti ................................ 601/33 X |

*Primary Examiner*—Linda C. M. Dvorak
*Attorney, Agent, or Firm*—Panitch Schwarze Jacobs & Nadel, P.C.

[57] ABSTRACT

A brace for applying a dynamic force to a jointed limb of a patient is provided. The brace includes a first brace portion adapted for connection to a first portion of a patient's limb on a first side of a joint in the limb, and a second brace portion adapted for connection to a second portion of the patient's limb on a second side of the joint. A pivotal connection is provided between the first and second brace portions, and is adapted to be generally aligned with the joint in the limb when the brace is attached to the patient's limb. A drive unit is connected to the first and second brace portions for imparting a moment on one of the first and second brace portions relative to the other of the first and second brace portions. A tension module is connected to the drive unit which imparts a dynamic, moment generating force on the drive unit.

16 Claims, 8 Drawing Sheets

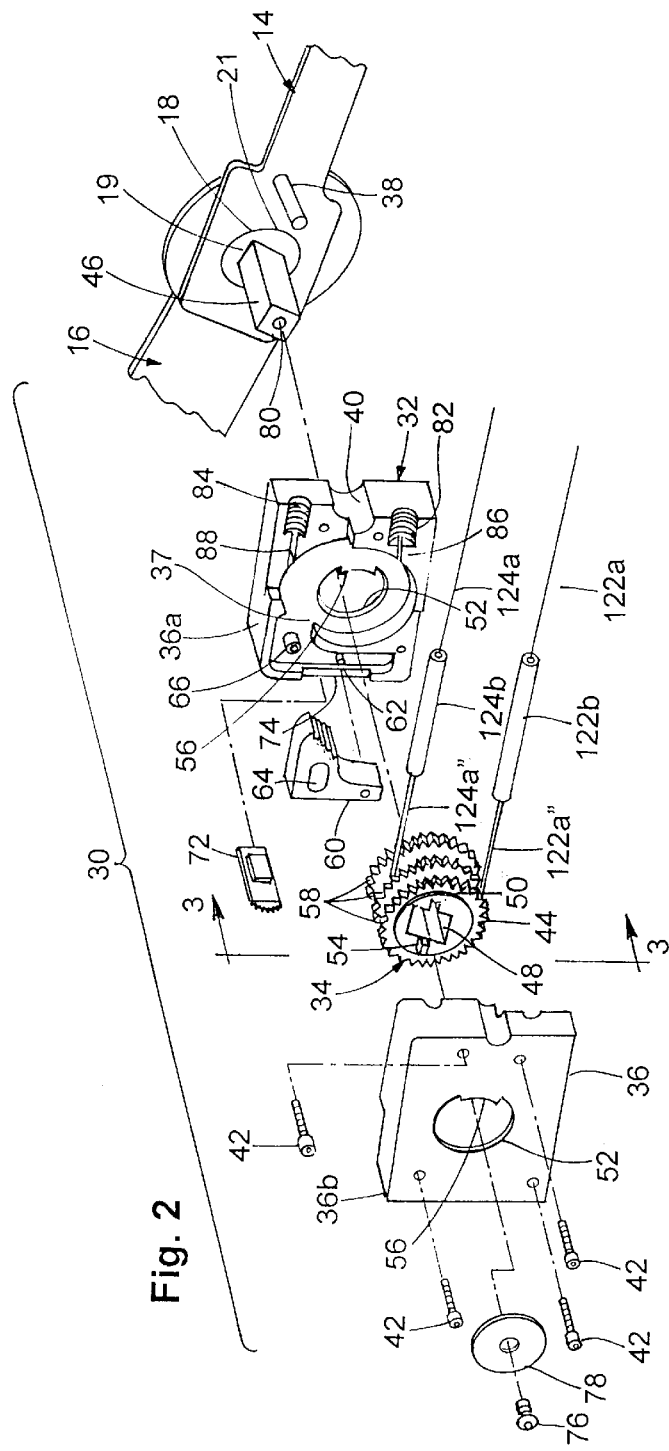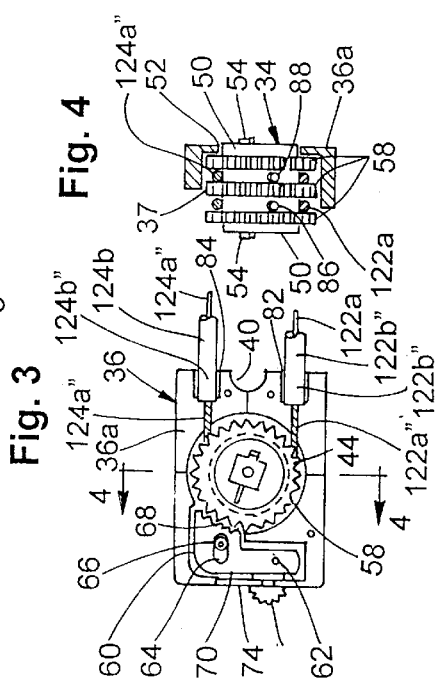

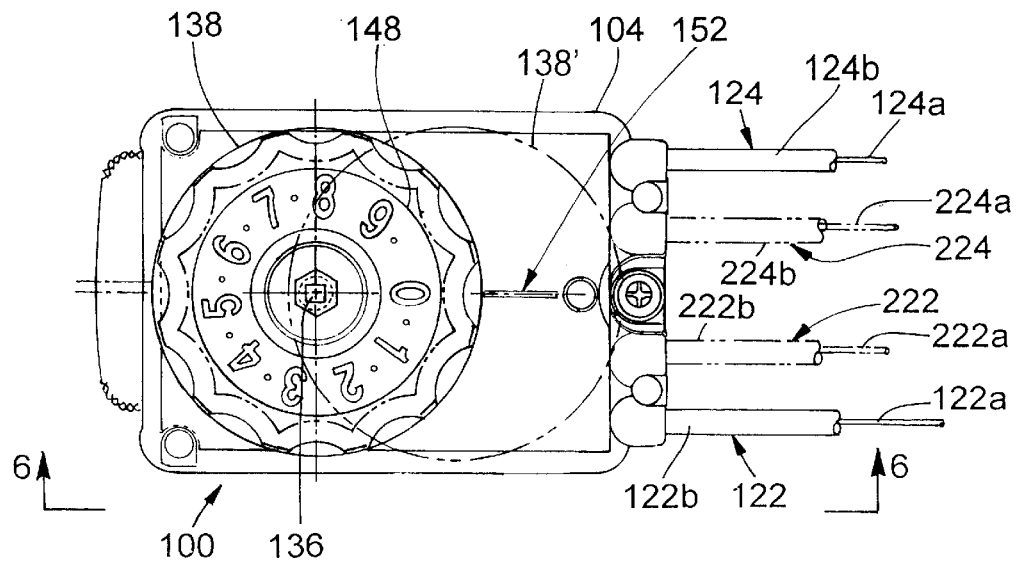
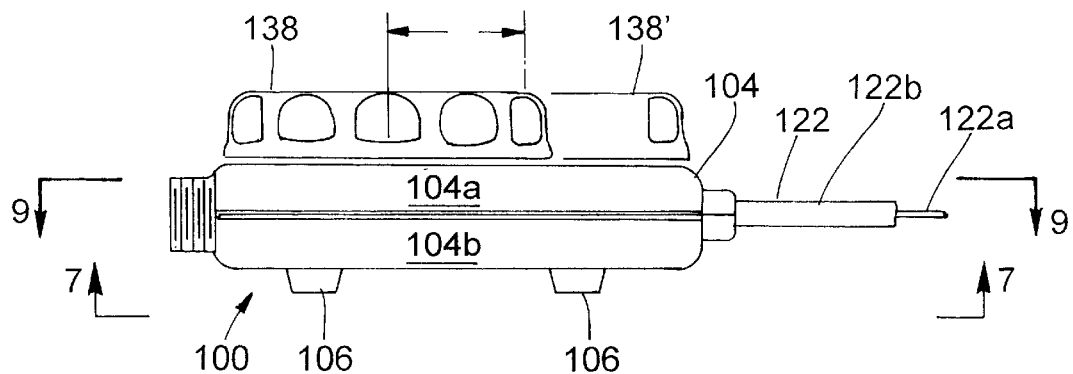
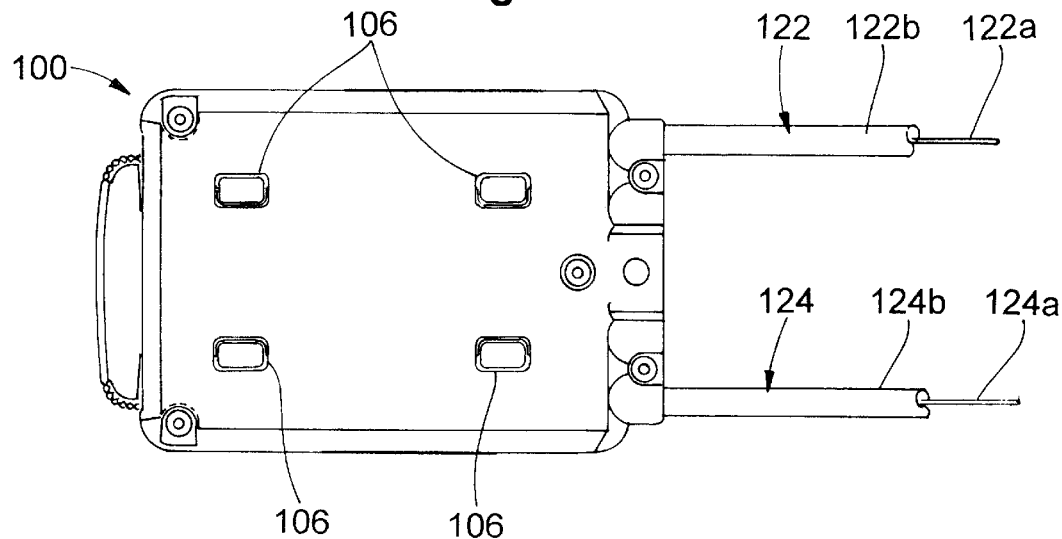

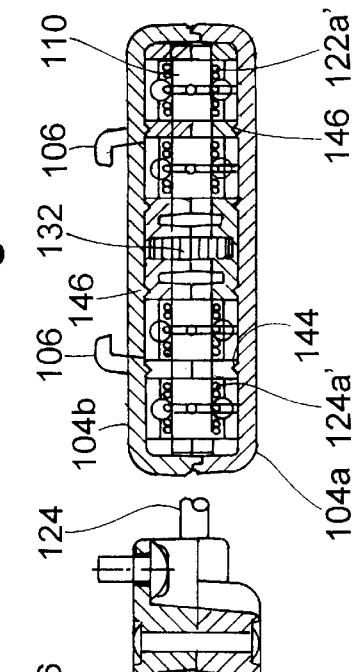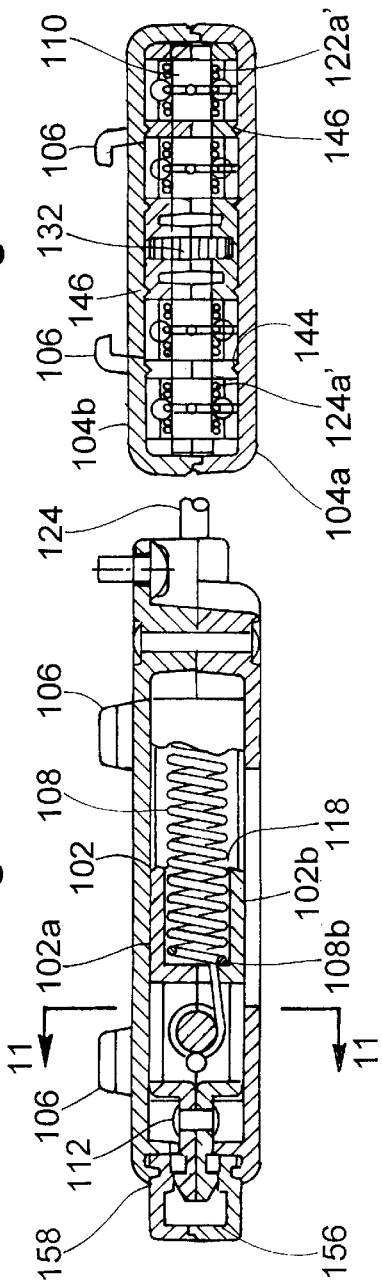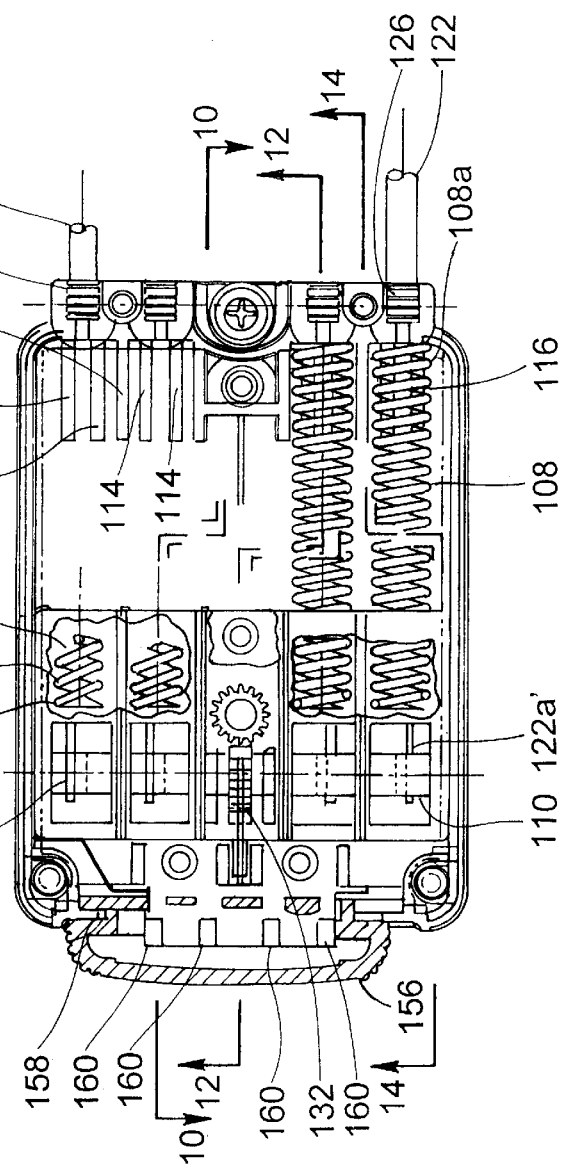

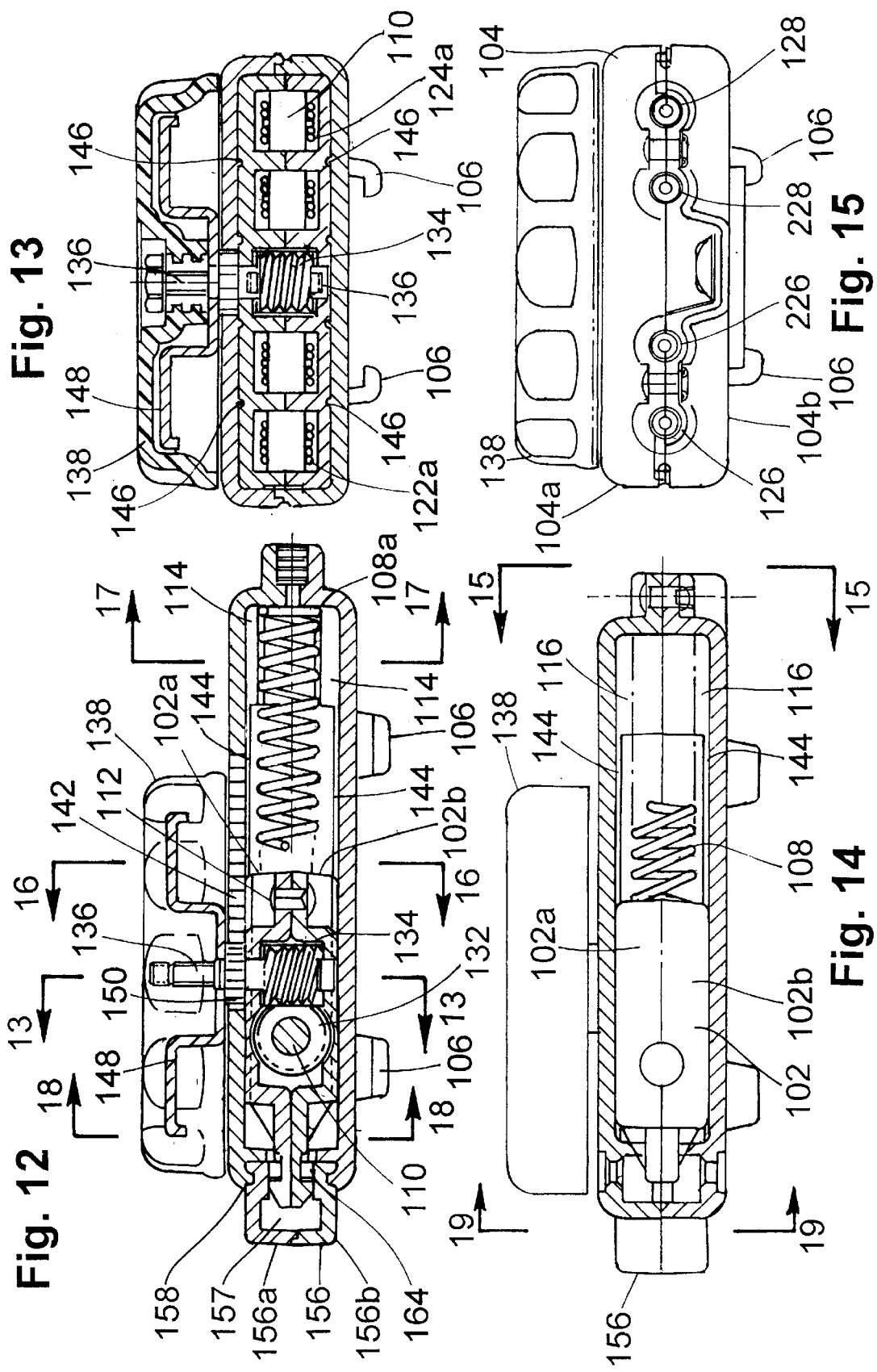

BRACE FOR APPLYING A DYNAMIC FORCE TO A JOINTED LIMB

BACKGROUND OF THE INVENTION

The present invention relates to a brace for a patient's limb, and more particularly, to a brace which is used to apply a dynamic force to a jointed limb to stretch contracted tissue and increase range of motion.

When a joint is immobilized for a period of time, such as when a patient's limb is immobilized in a cast or splint in order to allow a broken bone to heal, connected tissue at the joint tends to shorten, resulting in a decreased range of motion at the joint. This condition is exacerbated based on the length of time which the joint is immobilized.

As referred to herein, connective tissue includes ligaments, tendons, joint capsules, and other related structures which are composed of collagenous and reticular fibers, elastic fibers, fibrin and ground substance. These components form a mesh work of attached fibers which are connected at intervals throughout the tissue, and the longer the distance between the points of attachment, the greater the range of motion. The attachments can release or shift in response to prolong tension, or additional attachments can develop at points of prolong contact. The length of the fibers between the attachments can also increase or decrease depending on the presence or absence of force.

The prior known devices include variable locking devices with turn buckles, screws or hanging weights on the patient to apply a force on the limb. Recently, dynamic splints have been developed which use rubber bands or coil springs to apply a force on the splint at the joint. The dynamic splints are worn over a period of time, such as when a patient is sleeping, in order to stretch the connected tissue by providing a prolonged, constant, low intensity stretching in order to develop the patient's full range of motion.

In one known device, the brace comprises two sections attached on either side of the joint and a spring tension device is connected directly to the joint to apply a spring tension force on the patient's limb. However, it can be difficult for the patient to access or adjust the spring tension device while the device is being worn, especially for arm braces.

Another similar device utilizes coil springs as the connection between two sections of a brace to provide a resistance force to motion.

In another known device, two cuffs are provided for attachment to a patient's limb with a tower attached between the two cuffs to provide a mechanical advantage for increasing range of motion of the joint. The tower is a box-like structure which includes a drive mechanism for loading and unloading the cuffs to apply force to the limb. However, the tower device is fairly large and may not be suited for long term wear by a patient, such as when a patient is sleeping.

It is also known in the art to put a rigid element including a turn buckle on the inside angle of a joint between two cuffs attached on either side of a joint of a patient's limb and use the turn buckle to vary the length to push or pull the limb segments relative to each other.

It would be desirable to provide a device which can be worn by a patient for a long period of time, such as overnight while the patient sleeps, which provides an adjustable, controlled amount of force to the limb to allow for a gradual stretching action. It would also be desirable to use a force adjusting mechanism which does not have to be reconfigured to apply a force in the opposite direction, such as when a joint must be worked in both directions to regain the full range of motion. Additionally, it would be advantageous to provide a device in which the location of the force applying mechanism can be adjusted to a position where it is easily accessible for adjustment by the patient or in a position where it will cause the least patient discomfort.

SUMMARY OF THE INVENTION

Briefly stated, the present invention is a brace for applying a dynamic force to a jointed limb of a patient. The brace comprises a first brace portion which is adapted for connection to a first portion of a patient's limb on a first side of a joint in the limb. A second brace portion is provided which is adapted for connection to a second portion of the patient's limb on a second side of the joint. A pivotable connection is provided between the first and second brace portions. The pivotable connection is adapted to be generally aligned with the joint in the patient's limb when the brace is attached to the patient's limb. A drive unit is connected to the first and second brace portions for imparting a moment on one of the first and second brace portions relative to the other of the first and second brace portions. A tension module is provide which is responsive to relative motions between the first and second brace portions and is connected to the drive unit. The tension module imparts a dynamic, moment generating force on the drive unit when the first and second brace portions are substantially stationary with respect to each other.

In another aspect, the present invention provides a brace for applying a dynamic force to a jointed limb of a patient. The brace comprises a first brace portion adapted for connection to a first portion of a patient's limb on a first side of a joint in the limb. A second brace portion is adapted for connection to a second portion of the patient's limb on a second side of the joint. A pivotal connection is provided between the first and second brace portions. The pivotal connection is adapted to be generally aligned with the joint in the patient's limb when the brace is attached to the patient's limb. A tension module is provided which includes a slider mounted for sliding movement against a resilient force, and at least one resilient element is provided in contact with the slider for generating the resilient force. A rotatable shaft is mounted on the slider. First and second cable assemblies, each having a movable inner cable having first and second ends are provided. The first ends of the first and second movable inner cables are wound on the shaft, with the first movable inner cable of the first cable assembly being wound in a clockwise direction on the shaft and the second movable inner cable of the second cable assembly being wound in a counter-clockwise direction on the shaft. A first drive module is provided having a first part attached to one of the first and second brace portions and a second part, which is movable with respect to the first part, attached to the other of the first and second brace portions. The second ends of the movable inner cables are attached to the second part such that rotation of the rotatable shaft in a clockwise direction applies a dynamic tension force on one of the inner cables by moving the slider against the resilient force. The dynamic tension force on the one of the first and second inner cables is transferred to the second part of the drive module to impart one of a clockwise moment and a counter-clockwise moment on the first brace portion relative to the second brace portion. Rotation of the rotatable shaft in a counter-clockwise direction applies a dynamic tension force on the other of the first and second inner cables. The dynamic tension force on the other of the inner cables is transferred to the second part of the first drive module to impart a counter-clockwise moment on the first brace portion relative to the second brace portion.

In another aspect, the present invention provides a method of applying a dynamic force to a patient's limb to stretch contracted the tissue. The method comprises the steps of:

(a) positioning a brace having a first brace portion pivotally connected to a second brace portion such that the first brace portion is adapted for connection to a first portion of a patient's limb on a first side of a joint in the limb and the second brace portion is adapted for connection to a second portion of the patient's limb on a second side of the joint;

(b) rotating a shaft in one of a clockwise and a counter-clockwise direction, the shaft being connected to a slider mounted in a tension module for movement against a resilient force, the rotation of the shaft creating a dynamic tension force in one of a first movable inner cable and a second movable inner cable wound around the shaft, the first movable inner cable being wound in a clockwise direction around the shaft and the second movable inner cable being wound in a counter-clockwise direction around the shaft, rotation of the shaft causing one of the first and second movable inner cables to wind up on the shaft moving the slider against the resilient force; and (c) applying a moment in one of a clockwise and a counter-clockwise direction on the first brace portion relative to the second brace portion via the one of the first and second movable inner cables which is being wound upon the shaft acting on a drive unit, the drive unit having a first part fixed to the first brace portion and a second part fixed to the second brace portion, the first and second movable inner cables being attached to the second part such that the tension force on the one of the first and second inner cables resulting from rotation of the shaft is transferred to the second part of the first drive unit to impart one of a clockwise and a counter-clockwise moment on the first brace portion relative to the second brace portion to apply a dynamic load to the patient's limb to stretch the contracted tissue.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. The drawings are for the purpose of illustrating the present invention which is not limited to the devices and instrumentalities shown.

In the drawings:

FIG. 2 is a perspective view, partially disassembled, of the drive unit for the brace for applying a dynamic force to a jointed limb shown in FIG. 1;

FIG. 3 is a view, partially assembled, taken along lines 3—3 in FIG. 2;

FIG. 4 is a cross-sectional view taken along lines 4—4 in FIG. 3;

FIG. 5 is a top plan view of the tension module taken along lines 5—5 in FIG. 1;

FIG. 6 is a front elevational view of the tension module taken along lines 6—6 in FIG. 5;

FIG. 7 is a bottom plan view of the tension module taken along lines 7—7 in FIG. 6;

FIG. 9 is a plan view of the tension module, partially in cross-section, taken along lines 9—9 in FIG. 6;

FIG. 10 is a cross-sectional view of the tension module taken along lines 10—10 in FIG. 9;

FIG. 11 is a cross-sectional view of the tension module taken along lines 11—11 in FIG. 10;

FIG. 12 is a cross-sectional view of the tension module taken along lines 12—12 in FIG. 9;

FIG. 13 is a cross-sectional view of the tension module taken along lines 13—13 in FIG. 12;

FIG. 14 is a cross-sectional view of the tension module taken along lines 14—14 in FIG. 9;

FIG. 15 is a right side elevational view of the tension module taken along lines 15—15 in FIG. 14;

DETAILED DESCRIPTION OF THE INVENTION

Figure 1:
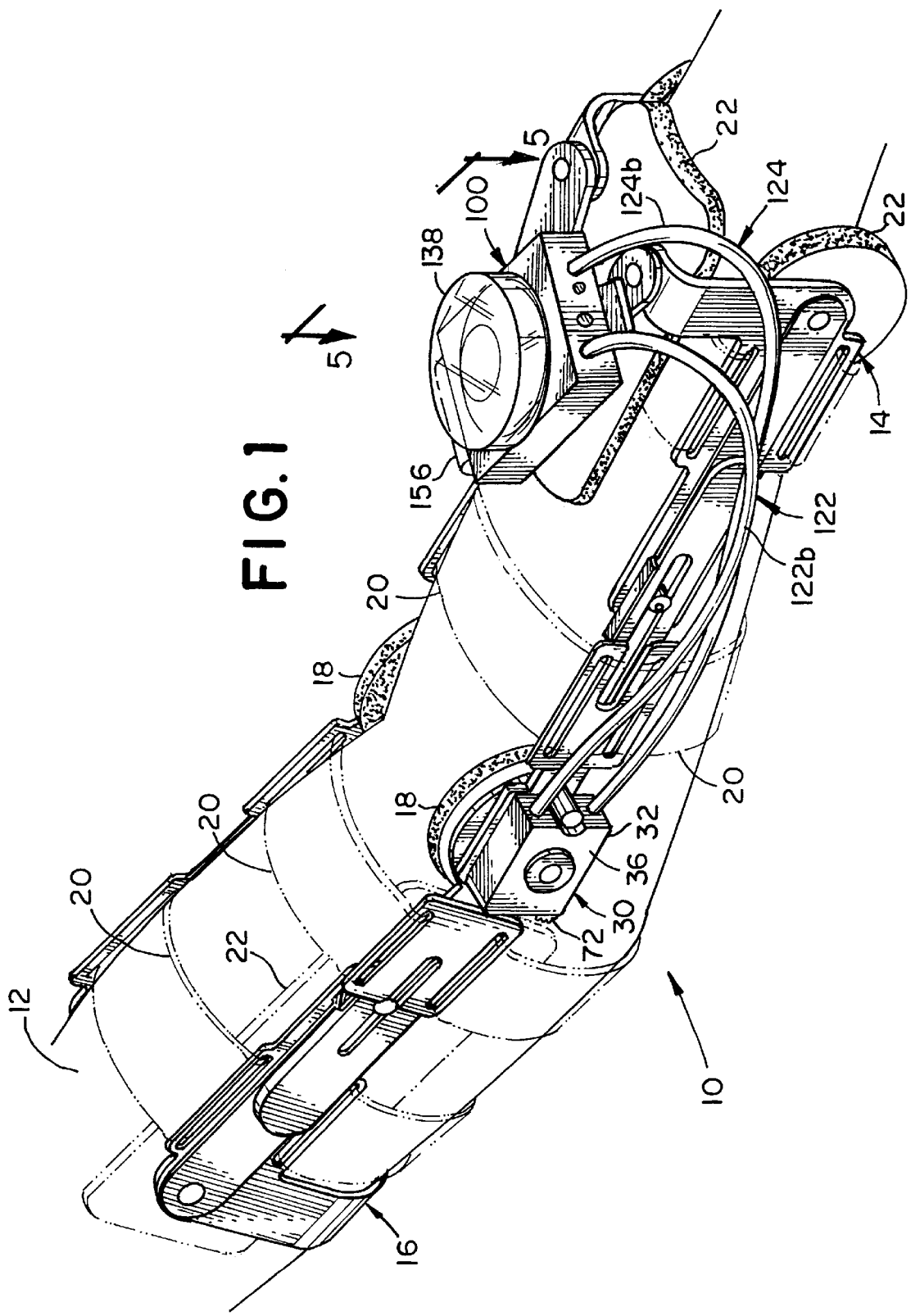
FIG. 1 is a perspective view of a brace for applying a dynamic force to a jointed limb of a patient in accordance with the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the brace 10 for applying a dynamic force to a jointed limb and designated parts thereof. The terminology includes the words above specifically mentioned, derivatives thereof and words of similar import.

Referring to the drawings, wherein like numerals indicate like elements throughout, there is shown in FIG. 1 a brace 10 for applying a dynamic force to a jointed limb 12 of a patient (not shown). The brace 10 includes a first brace portion 14 adapted for connection to a first portion of a patient's limb 12 on a first side of a joint in the limb 12. A second brace portion 16 adapted for connection to a second portion of the patient's limb 12 on a second side of the joint is also provided. The first and second brace portions 14, 16 are connected together at a pivotal connection 18 which is adapted to be generally aligned with the joint in the limb 12 when the brace 10 is attached to the patient's limb 12.

Preferably, the first and second brace portions 14, 16 are made of a strong, lightweight material, such as aluminum and are adapted to be adjusted to fit a particular patient's arm. Preferably, the first and second brace portions 14, 16 are attached to the patient's limb using straps (shown in phantom) which are connected together with VELCRO™ textile fastening material or a similar releasable fastening material to allow a patient to removably attach the first and second brace portions 14, 16 in position. Additionally, cushioned inserts 22 are provided between the first and second brace portions 14, 16 and the patient's limb 12 in order to prevent chafing and to provide for the patient's comfort. Preferably, the first and second brace portions 14, 16 extend on both sides of the patient's limb and the pivotal connection 18 is on either side of the joint to provide better stability. However, it will be recognized by those skilled in the art from the present disclosure that the pivotal connection could be provided on only one side of the joint, if desired.

As shown in FIG. 2, the pivotal connection 18 between the first and second brace portion 14, 16 preferably includes a polymeric bearing 19 which is attached to the second brace portion 16 around a post 46 which extends outwardly from the second brace portion 16. The bearing 19 is located within a corresponding opening 21 in the first brace portion 14 to provide for smooth pivotal movement between the first and second brace portions 14, 16. However, it will be recognized by those skilled in the art from the present disclosure that any type of pivotal connection can be used within the scope of the present invention, such as a pinned or articulated connection.

In the first preferred embodiment, the brace 10 is adapted to be attached to a patient's arm with the first brace portion 14 being connected to the forearm and the second brace portion 16 being connected around the bicep and tricep area. The pivotal connection 18 between the first and second brace portions 14, 16 is aligned with the patient's elbow. However, it will be recognized by those skilled in the art from the present disclosure that the brace 10 could be applied on either side of a patient's wrist, or could be applied to a patient's leg around the knee joint or the ankle, if desired. The first and second brace portions 14 and 16 would be sized for the specific application, with the pivotal connection 18 being aligned in each case with the joint. The brace 10 could also be applied to non-humans, such as an ape or a monkey.

Referring to FIGS. 1–4, a drive unit 30 is connected to the first and second brace portions 14, 16 for imparting a moment on one of the first and second brace portions 14, 16 relative to the other of the first and second brace portions 14, 16. The drive unit 30 has a first part 32 which is attached to one of the first and second brace portions 14, 16, and a second part 34, which is movable with respect to the first part 32, attached to the other of the first and second brace portions 14, 16. As shown in FIG. 2, preferably the first part 32 of the first drive unit 30 comprises the housing 36 which includes an inner half 36a and an outer half 36b. The housing 36 is connected to the first brace portion 14 at the pivotal connection 18 by the post 46 which extends from the second brace portion, and a pin 38 which is connected to the first brace portion 14 and is located within a corresponding recess 40 in the housing 36 when the drive unit 30 is installed. The housing 36 includes a cavity 37 defined between the inner and outer halves 36a, 36b when they are assembled together.

Still with reference to FIGS. 2 through 4, the second part 34 of the first drive unit 30 preferably comprises a two-sheave pulley 44 which is located within the cavity 37 in the housing 36. The two-sheave pulley 44 is connected to the second brace portion 16 by the post 46. The post 46 preferably has a generally square cross-section which is complementary to an aperture 48 defined through the center of the two-sheave pulley 44. Preferably, circular bosses 50 are provided on each side of the two-sheave pulley 44 which ride in corresponding openings 52 in the inner and outer halves 36a, 36b of the housing 36 on opposite sides of the cavity 37.

Motion limiting stops 54 are located on either side of the two-sheave pulley 44 on the circular bosses 50 and are adapted to contact corresponding stops 56 located in the openings 52 in the inner and outer housing halves 36a, 36b.

The drive unit 30 includes a locking mechanism for locking the first part 32 relative to the second part 34. The outer periphery of the two-sheave pulley 44 includes at least one row of teeth 58, and in the preferred embodiment, three rows of teeth 58 are provided. A lock element is located on the drive unit 30, preferably within the housing 36, for fixing the position of the first part 32 relative to the second part 34. As shown in detail in FIGS. 2 and 3, the lock element comprises a pawl 60 pivotably mounted on a pin 62 in the housing 36. A slot 64 is defined in the pawl 60. A second pin 66 extends from the inner part 36a of the housing 36 into the slot 64 to limit the movement of the pawl 60. Preferably, the pawl 60 includes a toothed surface 68 located in a position adjacent to the rows of teeth 58 on the two-sheave pulley 44. The opposite surface 70 of the pawl 60 from the toothed surface 68 is tapered outwardly. A slider 72 is positioned adjacent to the tapered surface 70 and is movably mounted in a slot 74 defined in the inner and outer parts 36a, 36b of the housing 36. As the slider 72 is moved upwardly from the bottom area of the slot 70, as shown in FIG. 3, it contacts the tapered surface 70 of the pawl 60, causing the pawl 60 to pivot about the pin 62, forcing the toothed surface 68 of the pawl 60 to engage with the rows of teeth 58 on the outer periphery of the two sheave pulley 44 to lock the two-sheave pulley 44 in a fixed position with respect to the housing 36.

As shown in detail in FIG. 2, the inner and outer halves 36a, 36b of the housing 36 are connected together using screws 42 which are inserted through corresponding apertures in the outer part 36b of the housing 36 and threadedly engaged in corresponding apertures in the inner part 36a of the housing 36. A screw 76 is inserted through a washer 78 and engaged in a threaded aperture 80 located in the post 46 attached to the second brace portion 16 to secure the drive unit 30 to the first and second brace portions 14, 16.

In the first preferred embodiment the drive unit housing 36 is made from aluminum and the two-sheave pulley 44 and pawl 60 are made of steel. However, it will be recognized by those skilled in the art from the present disclosure that the housing 36 could be made from other suitable metallic or polymeric materials, such as steel, brass, PVC or any other material having the desired strength. The two-sheave pulley 44 and pawl 60 can also be made from other suitable materials, such as those disclosed above.

Figure 8:
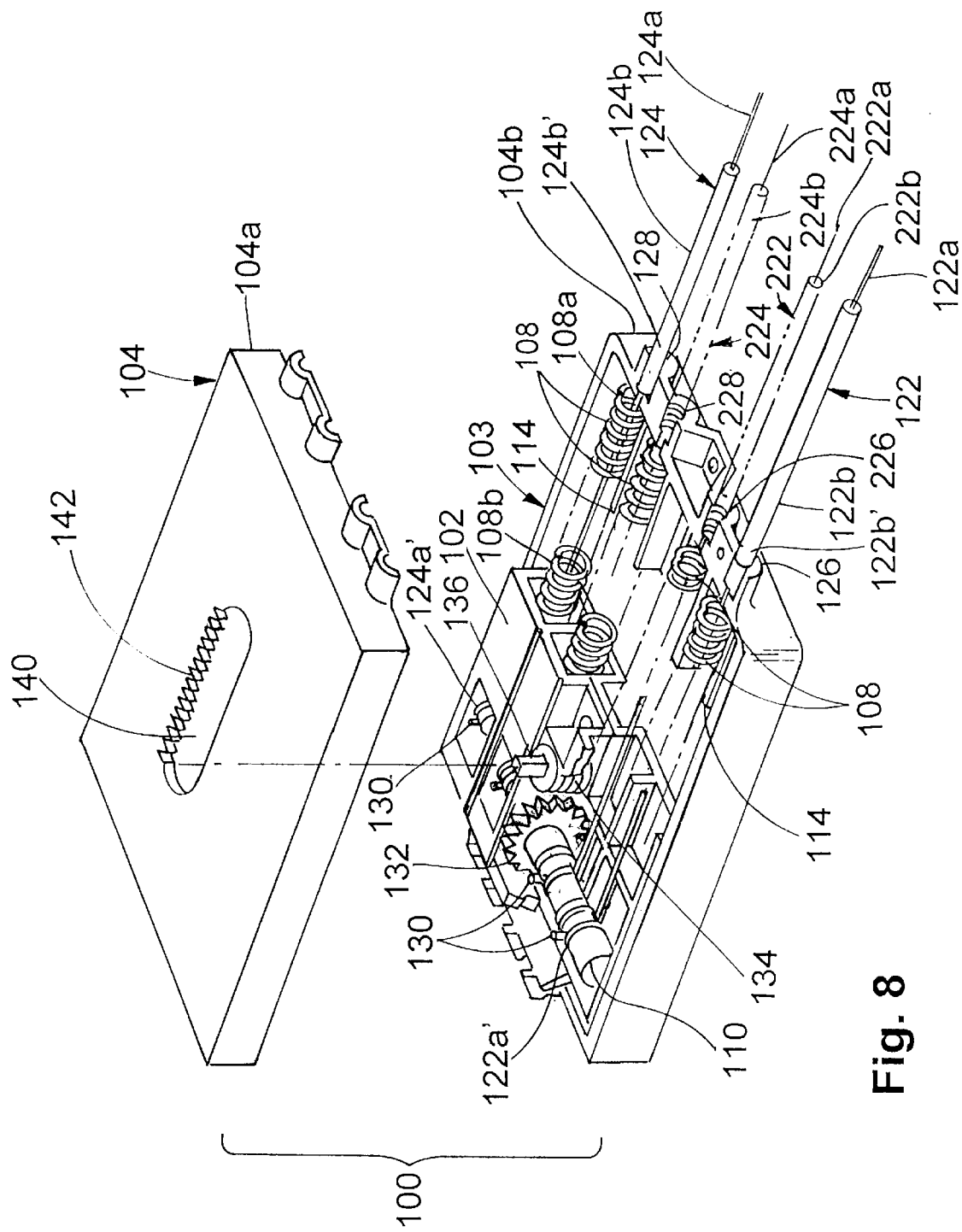
FIG. 8 is a partially disassembled perspective view, partially broken away, of the tension module shown in FIGS. 5–7 for the brace for applying a dynamic force to a jointed limb shown in FIG. 1.
Figure 16:
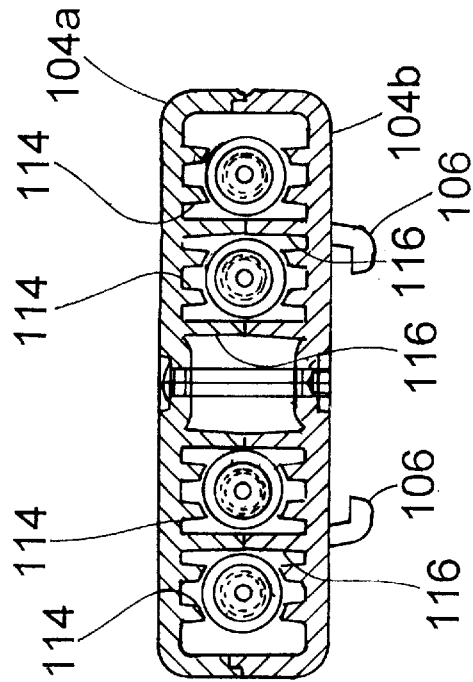
FIG. 16 is a cross-sectional view of the tension module taken along lines 16—16 in FIG. 12.
Figure 17:
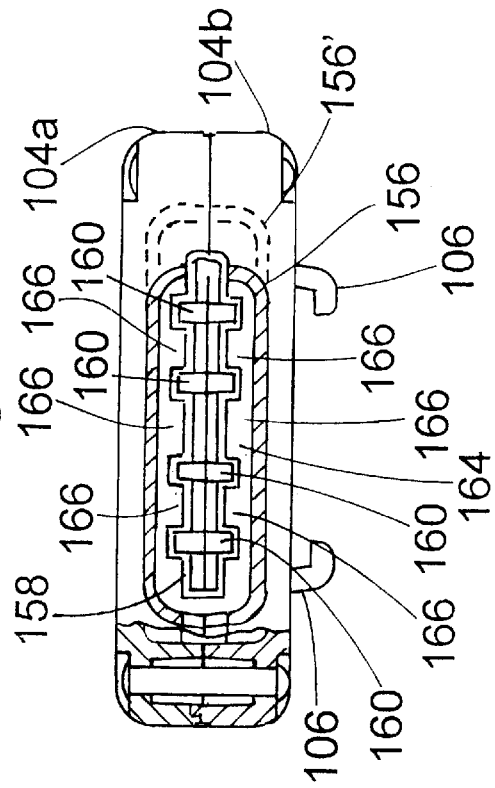
FIG. 17 is a cross-sectional view of the tension module taken along lines 17—17 in FIG. 12.
Figure 18:
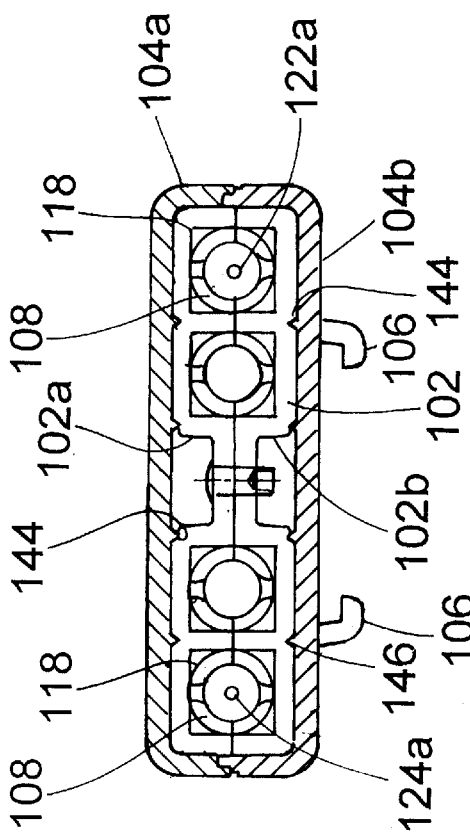
FIG. 18 is a cross-sectional view of the tension module taken along lines 18—18 in FIG. 12.
Figure 19:
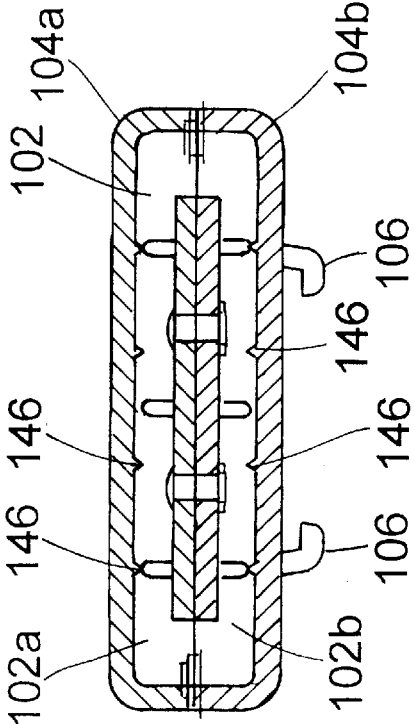
FIG. 19 is a cross-sectional view of the tension module taken along lines 19—19 in FIG. 14.

Referring now to FIG. 1, a tension module 100 is connected to the first drive unit 30 and imparts a dynamic, moment generating force on the first drive unit 30. As shown in FIG. 8, the tension module includes a slider 102 mounted within a cavity 103 in a housing 104 having upper and lower halves 104a, 104b, shown in detail in FIGS. 5–8. The slider 102 is mounted for sliding movement against a resilient force. Preferably, the resilient force is generated by at least one resilient element in contact with the slider 102. In the preferred embodiment, the at least one resilient element is a coil spring 108 and preferably four coil springs 108 are provided. However, it will be recognized by those skilled in the art from the present disclosure that other types of resilient elements, such as an elastomeric block, tension springs, air springs, or any other type of resilient force generating element can be used.

As shown in FIG. 8, where the slider 102 is partially broken away, a rotatable shaft 110 is mounted on the slider 102. As best seen from FIGS. 9, 10 and 12, the slider 102 is made from upper and lower halves 102a, 102b which are fastened together about the shaft 110 to secure the shaft 110 in position in the slider 102. Preferably, the upper and lower halves 102a, 102b of the slider are fastened together with mechanical fasteners, such as rivets 112. However, it will be recognized by those skilled in the art from the present disclosure that other fastening means, such as welds or spring clips could be used, if desired.

As shown in FIGS. 8, 9, 12 and 14, the housing 104 includes guide members 114 located in the cavity 103 for holding the first end 108a of each spring 108 in position. Dividing walls 116 are formed in the upper and lower halves 104a, 104b of the housing 104 which separate the first ends 108a of the springs 108 from the adjacent springs 108. Preferably, pockets 118 are formed in the slider 102 for receiving the second ends 108b of the springs 108. It will be recognized by those skilled in the art from the present disclosure that the spring guides 114, dividing walls 116 and pockets 118 may be omitted if desired.

Referring to FIGS. 1–3 and 5–9, first and second cable assemblies 122, 124 are shown. Each cable assembly has a movable inner cable 122a, 124a, and preferably includes an outer sheath 122b, 124b. Each of the first and second movable inner cables 122a, 124a includes a first end 122a', 124a' and second end 122a", 124a". The first ends 122a', 124a' of the first and second movable inner cables 122a, 124a are wound on the shaft 110, as shown in FIGS. 9–11. The first movable inner cable 122a of the first cable assembly 122 is wound in a clockwise direction on the shaft 110 and the second movable inner cable 124a is wound in a counter-clockwise direction on the shaft 110.

Cable assemblies having an inner cable 122a, 124a slidably disposed within an outer sheath 122b, 124b are known in the art, and typically comprise a metallic inner cable and a protective outer sheath made of a polymeric material. However, other types of push-pull cable assemblies or linkages for transmitting force, such as hydraulic lines, may be used in conjunction with the present invention, if desired.

As shown in FIG. 8, preferably the first ends 122a', 124a' of the first and second movable inner cables 122a, 124a are threaded through respective openings 126, 128 in the housing which are axially aligned with the springs 108. The movable inner cables 122a, 124a each pass through the open interior space of a respective spring 108 and into the slider 102 where they pass through the pocket 118 and an opening which leads to the shaft 110. The movable inner cables 122a, 124a are fastened to the shaft 110 using cross pins 130.

The outer sheaths 122b, 124b of the cable assemblies 122, 124 also have first ends 122b', 124b' and second ends 122b", 124b". The first ends 122b', 124b' of the outer sheaths 122b, 124b are affixed to the housing 104 of the tension module 100. Preferably, the housing 104 includes serrations or threads in the openings 126, 128 which engage the first ends 122b', 124b' of the outer sheaths 122b, 124b to firmly secure the first ends 122b', 124b' of the outer sheath 122b, 124b to the housing 104 when the housing halves 104a, 104b are assembled.

Referring to FIGS. 2, 3 and 4, the second ends 122a", 124a" of the movable inner cables 122a, 124a are attached to the second part 34 of the first drive unit 30. The first movable inner cable 122a is wound in one of a clockwise and a counter-clockwise direction on one of the two sheaves of the two sheave pulley 44 which comprises the second part 34 of the first drive unit 30. As shown in FIGS. 2 and 3, the first movable inner cable 122a is preferably wound in a clockwise direction such that as tension is applied to the second inner cable 122a, the two sheave pulley 44 tends to unwind in a counter-clockwise direction. The second movable inner cable 124a is wound in the other of the clockwise and counter-clockwise directions on the other of the two sheaves of the two sheave pulley 44, and is preferably wound in the counter-clockwise direction such that as tension is applied to the second movable inner cable 124a, the two sheave pulley 44 is turned in a clockwise direction as the second movable inner cable 124a unwinds. Preferably, the first and second movable inner cable 122a, 124a are anchored in apertures 86, 88 in the two sheave pulley 44.

Referring to FIGS. 1–3 and 8, rotation of the rotatable shaft 110 in a clockwise direction applies a tension force on one of the inner cables, and in the preferred embodiment, on the first inner cable 122a. If the first and second brace portions 14, 16 are free to rotate relative to each other, the tension force on the one of the first and second inner cables causes the two-sheave pulley 44 to rotate in a clockwise or counter-clockwise direction, and in the preferred embodiment in a counter-clockwise direction. However, if resistance to movement is encountered, the two-sheave pulley stops turning, and the first end 122a', 124a' of the one of the first and second movable inner cables 122a, 124a winds on the shaft 110, moving the slider 102 against the resilient force generated by the springs 108 to create a dynamic tension force on the first movable inner cable 122a. The dynamic tension force on the one of the inner cables 122a, 124a, and in the preferred embodiment the first inner cable 122a, is transferred to the second part 34 of the first drive unit 30 to impart one of a clockwise moment and a counter-clockwise moment on the first brace portion 14 relative to the second brace portion 16, and in the preferred embodiment a counter-clockwise moment. Rotation of the rotatable shaft 110 in a counter-clockwise direction applies a dynamic tension force on the other of the first and second inner cables 122a, 124a, preferably the second inner cable 124a. The dynamic tension force on the other of the first and second inner cables 122a, 124a, preferably the second inner cable 124a, is transferred to the second part 34 of the drive unit 30 to impart the other of the clockwise moment and the counter-clockwise moment on the first brace portion 14 relative to the second brace portion 16, and preferably imparts a clockwise moment. The strength of the springs 108 can be selected to provide a desired force level for therapy.

As shown in FIGS. 2–4, the second ends 122b", 124b" of the outer sheaths 122b, 124b are affixed to the first part 32 of the first drive unit 30 by serrated openings 82, 84 located in the inner and outer housing halves 36a, 36b. As the inner and outer housing halves 36a, 36b are assembled, the second ends 122b", 124b" of the outer sheaths 122b, 124b are securely clamped in the serrated openings 82, 84, with the movable inner cables 122a, 124a passing through slots 86, 88 from the serrated openings 82, 84 into the two-sheave pulley 44 containing cavity 37 within the housing 36.

While the first and second parts 32, 34 of the first drive unit 30 are a housing 36 and a two-sheave pulley 44 in the first preferred embodiment, it will be recognized by those skilled in the art from the present invention that other two-directional drive arrangements could be used, such as a gear and rack arrangement in which the gear is used to displace a rack to cause relative movement between the two brace portions 14, 16. Other suitable bi-directional drive arrangements can also be used, such as a hydraulically actuated cylinder, if desired.

Referring now to FIGS. 8, 12 and 13, a gear 132 is located on the rotatable shaft 110. A worm 134 mounted on the slider 102 via a shaft 136 is drivingly engaged with the gear 132.

The worm 134 is actuatable by a control knob 138 attached to the shaft 136. The control knob 138 is keyed to the shaft 136 such that rotation of the control knob 138 results in a corresponding rotation of the shaft 136.

In the preferred embodiment the worm 134 and the gear 132 are made of a metallic material, such as brass or steel, and the shaft 110 is made of steel. However, it will be recognized by those skilled in the art from the present disclosure that other suitable materials having sufficient strength can be used, if desired.

The control knob 138 and the shaft 136 extend through a slot 140 in the housing 104, shown most clearly in FIGS. 8 and 12. The slot 140 extends parallel to a direction of travel of the slider 102 to allow the control knob 138 to move with the slider 102.

Referring to FIGS. 12–15, preferably, the slider 102 is made of a high strength metallic material, such as aluminum or steel and is made from the two halves 102a, 102b which are connected together using rivets or other mechanical fasteners, as shown in FIGS. 9, 12, 16 and 18. However, it will be recognized by those skilled in the art from the present disclosure that the slider could be made of other suitable materials which can be cast, machined or otherwise formed to the proper configuration.

Preferably, the lower portion 104b of the housing 104 includes clips 106 for connecting the tension module to the brace, or to another remote location. However, it will be recognized by those skilled in the art from the present disclosure that the clips 106 can be omitted if desired.

As best shown in FIGS. 11–13, preferably the inside of the housing 104 includes inwardly protruding parallel tracks 144, and the slider 102 includes corresponding grooves 146 for controlling the direction of movement of the slider 102. This insures that the slider 102 will not become canted or bind due to uneven loading as the dynamic tension force is applied. Preferably, a suitable lubricant, such as lithium grease, is provided to insure smooth sliding of the slider 102 within the housing 104. However, it will be recognized by those skilled in the art from the present disclosure that a self-lubricating bearing material could be used on one or more surfaces of the slider 102 or on the inside of the housing 104 to insure smooth movement of the slider 102 relative to the housing 104.

Referring now to FIGS. 8 and 12, a row of teeth 142 are located along the slot 140. An indicator 148 is rotatably mounted to the slider 102 and extends through the slot 140 and engages the teeth 142 such that movement of the slider 102 causes the indicator 148 to change. Preferably, the indicator 148 is a dial having a gear 150 which engages the teeth 142 located along the slot 140 such that movement of the slider 102 causes the indicator dial 148 to rotate. The indicator dial 148 may include indicia, such as numbers as shown in FIG. 5, to indicate a relative amount of dynamic force which is being applied by the springs 108 based on the displacement of the slider 102.

Preferably, the indicator 148 is located coaxially with the control knob 138 on the shaft 136, with the indicator 148 being free to rotate independently of the shaft 136 and the control knob 138. In the preferred embodiment, the control knob 138 is made of a transparent polymeric material so that the indicia on the indicator 148 can be read.

As shown in FIGS. 5 and 6, rotation of the control knob 138 after the drive unit encounters resistance to further relative movement of the first and second brace portions 14, 16, or after the lock element 60 is engaged, results in movement of the control knob 138 (and the slider 102) from the position shown in FIGS. 5 and 6 to any one of a number of positions such as 138'. As the control knob 138 is rotated, a dynamic tension force is applied to one of the first and second movable inner cables 122a, 124a due to movement of the slider 102 against the resilient force of the springs 108. Movement of the slider 102 and the shaft 136 relative to the teeth 142 located along the slot 140 in the housing 104, causes the gear 150 engaged with the teeth 142 to rotate the indicator 148.

A marker line 152, shown in FIG. 5, is preferably provided on the surface of the upper part 104a of the housing 104 which can be used as a reference in connection with the indicia located on the indicator dial 148 for the amount of dynamic force being applied by the springs 108 to the slider 102.

Preferably, the tension module 100 is removably attached to one of the first and second brace portions 14, 16, and more preferably, the tension module 100 is mounted to the first brace portion 14 as shown in FIG. 1. In the preferred embodiment, the tension module 100 is mounted using VELCRO™ textile fastening strips, or any other similar type of releasable fastening material. Alternatively, the tension module 100 can be mounted using a quick release mechanical fastener or clip.

In the first preferred embodiment 10, the first and second cable assemblies 122, 124 are of a sufficient length such that the tension module 100 can be located remotely from the brace 10, if desired. For example, the cable assemblies 122, 124 can have a sufficient length to enable the tension module 100 to be mounted to a patient's belt or in another easily accessible location to allow the patient to adjust the control knob 138, as needed for therapy.

Preferably, the tension module 100 includes a locking element 156 for fixing the position of the slider 102 to prevent movement relative to the tension module 100. As shown in FIGS. 9, 10, 12, 18 and 19, the locking element 156 is slidably mounted in a slot 158 in the end of the housing 104. The end of the slider 102 adjacent to the locking element 156 includes four triangular shaped lugs 160 which protrude through the slot 158 in the housing 104. The locking element 156 includes a corresponding opening 164 and the triangular shape locking elements 160 extend outwardly from the housing 104 through the opening 164 and into a cavity 157 within the locking element 156. As the locking element 156 is moved sideways toward a second, locked position shown in phantom lines at 156' in FIG. 19, tangs 166 around the periphery of the opening 164 in the locking element 156 engage behind the triangular lugs 160 to lock the slider 102 in a fixed position.

Preferably, the locking element 156 is made of upper and lower halves 156a, 156b. Preferably, the locking element 156 is made of a cast or molded metallic material, such as aluminum, or an aluminum alloy. However, it will be recognized by those skilled in the art from the present disclosure that various other types of metallic materials such as steel or brass could be used, or suitable polymeric materials can be used, if desired.

In the first preferred embodiment 10, the upper and lower halves 104a, 104b of the housing 104 are made from a metallic material, such as aluminum or steel, and can be machined and/or cast and machined to the required configuration. The upper and lower housing halves 104a, 104b are assembled with screws (not shown) after the above-noted components have been installed within the cavity 103.

Figure 20:
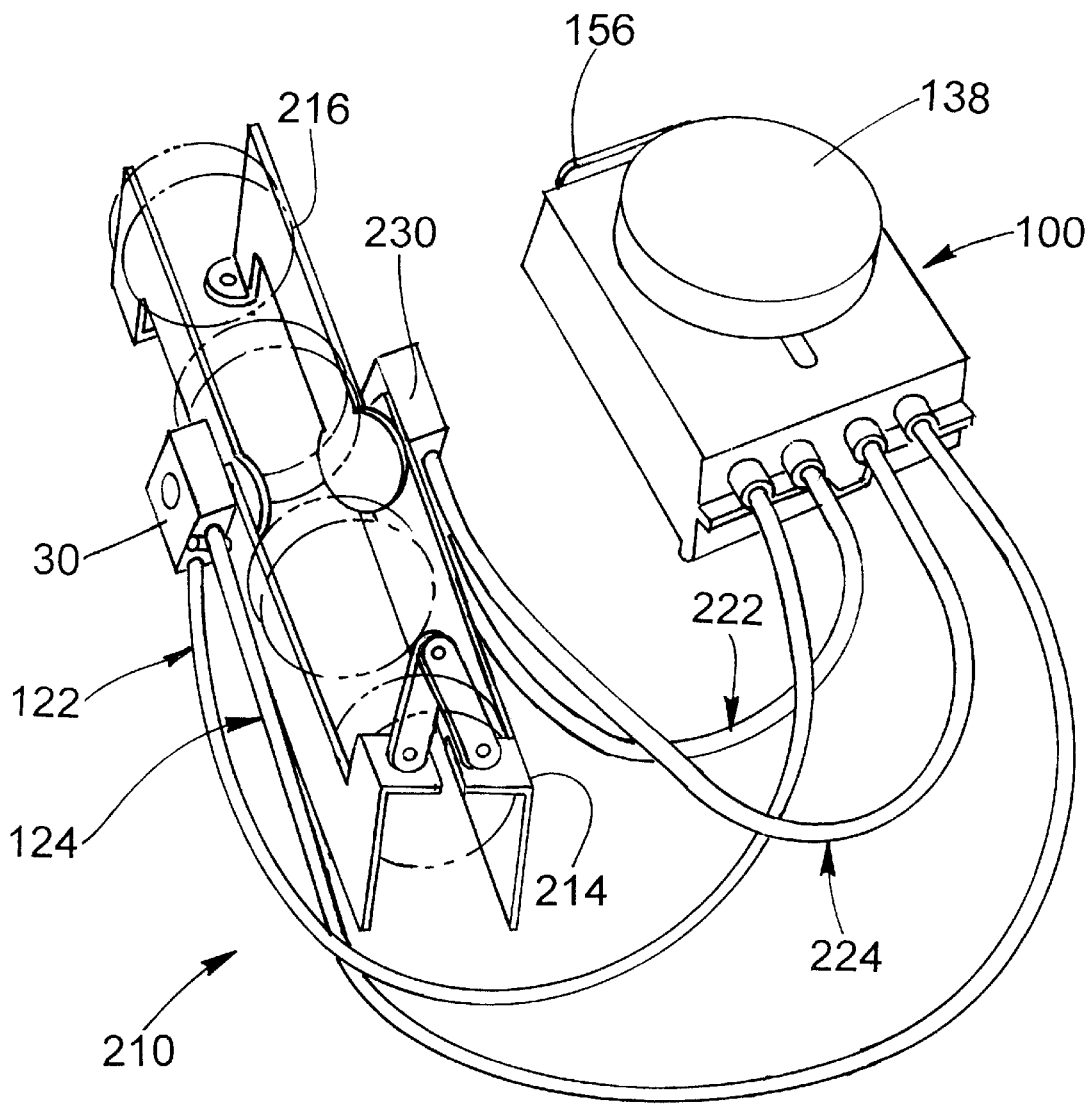
FIG. 20 is a perspective view of a second embodiment of a brace for applying a dynamic force to a limb of a patient in accordance with the present invention.

Referring now to FIG. 20, a second embodiment of the invention 210 is shown. The second embodiment 210 is similar to the first embodiment 10 and like elements have been identified with the same reference numerals. The differences between the first embodiment 10 and the second embodiment 210 are described in detail below.

In the second embodiment 210, a second drive unit 230 is attached on the opposite side of the joint from the first drive unit 30. The second drive unit 230 is identical to the first drive unit 30 and includes the first and second parts 32, 34 which are preferably the housing 36 and the two-sheave pulley 44, as previously described. The first part 32 of the second drive unit is connected to the first brace portion 214 and the second part 34 of the second drive unit 230 is connected to the second brace portion 216.

Third and fourth cable assemblies 222, 224 are connected between the tension module 100 and the second drive unit 230. The third and fourth cable assemblies 222, 224 are shown in phantom lines in FIGS. 5 and 8, and provisions are preferably provided in the tension module 100 for connection of the third and fourth cable assemblies 222, 224 to openings 226, 228, as shown in FIGS. 8 and 15.

The third and fourth cable assemblies 222, 224 are connected between the tension module 100 and the second drive unit 230. The third and fourth cable assemblies 222, 224 each have a movable inner cable 222a, 224a (shown in phantom lines in FIG. 5) and an outer sheath 222b, 224b. The movable inner cables 222a, 224a each have a first end and a second end which are similar to the first and second ends 122a', 124a', 122a", 124a" of the first and second movable cables 122a, 124a. The third and fourth outer sheaths 222b and 224b also include first and second ends similar to the first and second ends 122b', 124b', 122b", 124b" of the first and second outer sheaths 122b, 124b. Each movable inner cable 222a, 224a is slidably disposed within the respective outer sheath 222b, 224b. The first ends of the third and fourth movable inner cables 222a, 224a are wound on the shaft 110, with the third movable inner cable 222a of the third cable assembly 222 being wound in a clockwise direction, similar to the first movable inner cable 122a. The fourth movable inner cable 224a of the fourth cable assembly 224 is wound in a counter-clockwise direction on the shaft 110, similar to the second inner cable assembly 124.

The second ends of the third and fourth movable inner cables 222a, 224a are attached to the second part 34 of the second drive unit 230, which is preferably the two-sheave pulley 44, such that rotation of the rotatable shaft 110 in a clockwise direction supplies a dynamic tension force on one of the third and fourth inner cables 222a, 224a by moving the slider 102 against the resilient force. The dynamic tension force on the one of the third and fourth inner cables 222a, 224a is transferred to the second part 234 of the drive unit to impart one of a clockwise and a counter-clockwise moment on the first brace portion 214 relative to the second brace portion 216, and preferably imparts a counter-clockwise moment.

Rotation of the rotatable shaft 110 in a counter-clockwise direction applies a dynamic tension force on the other of the third and fourth inner cables 222a, 224a, along with the other of the first and second cables 122a, 124a, and the dynamic tension force on the other of the third and fourth inner cables is transferred to the second part 34 of the second drive unit 230 to impart the other of a clockwise and a counter-clockwise moment on the first brace portion 214 relative to the second brace portion 216, and preferably imparts a clockwise moment along with the first drive unit 30.

The construction of the second drive unit 230 is identical to the first drive unit 30, and the second part 34 of the second drive unit comprises the two-sheave pulley 44 which is rotatably located in the housing 36 of the second drive unit 230. The second end 222a" of the third movable inner cable 222a is wound in one of a clockwise and a counter-clockwise direction on one of the two sheaves of the pulley 44, and the second end 224a" of the fourth movable inner cable 224a is wound in the other of the clockwise and counter-clockwise directions on the other of the two sheaves.

Since the first and second drive units 30, 230 act on opposite sides of the joint, the force is more evenly applied to the patient's limb by the first and second brace portions 214, 216. The first and second drive units 30, 230 must be properly set up such that the dynamic tension force carried by the cable assemblies 122, 124 does not counteract the force carried by the cable assemblies 222, 224. However, this will be recognized by those skilled in the art, and can be easily corrected if the cables are reversed by switching the positions of the third and fourth cables 222, 224 at the connection to the second drive unit 230, if necessary.

The length of the cables 122, 124, 222, 224 can be varied as desired to allow the tension module 100 to be located in a convenient location for adjustment by the patient. However, it will be recognized by those skilled in the art from the present disclosure that some force is lost due to friction between the outer sheath 122b, 124b, 222b, 224b and the movable inner cables 122a, 124a, 222a, 224a and therefore the lengths of the cables should be only as long as needed for convenient positioning of the tension module 100 in order to avoid excessive losses.

It will be recognized by those skilled in the art from the present disclosure that the tension module could be provided with provisions for connection to additional drive units (not shown) if desired. It will be similarly recognized by the skilled artisan that the first and second drive units 30, 230 which are connected to a single tension module 100 could be used on braces attached to different limbs or attached at two joints on a single limb (such as a wrist and elbow) to provide dynamic tension therapy at both joints.

In operation, the brace 10 in accordance with the first preferred embodiment of the invention can be used for dynamic tension or static tension therapy. For dynamic tension therapy, a dynamic force is applied to the patient's limb 12 over a period of time to stretch contracted tissue. In order to apply the brace 10, it is first adjusted so that it can be positioned on the patient's limb 12. The position of the first brace portion 14 relative to the second brace portion 16 can be adjusted by locking the locking element 156 on the tension module 100 to prevent the slider 102 from moving within the housing 104. The slider 72 of the locking mechanism on the first drive unit 30 is moved to the downward position such that the toothed surface 68 of the pawl 60 does not engage the rows of teeth 58 on the two-sheave pulley 44. The patient then turns the control knob 138 in one of a clockwise or counter-clockwise direction to rotate the shaft 110. As the shaft rotates, one of the movable inner cables 122a, 124a is wound onto to the shaft and the other is unwound from the shaft 110, depending upon the direction of rotation. The force applied to one of the movable inner cables 122a, 124a being wound onto the shaft 110 is translated to the drive unit 30 and causes the second part 34 of the drive unit 30, which is preferably the two-sheave pulley 44, to rotate relative to the first part 32, which preferably comprises the housing 36. Once the brace portions 14, 16 are adjusted to the correct positions, the brace tension is applied to the patient.

As illustrated in FIG. 1, the brace 10 is preferably attached to the patient's arm on either side of the elbow joint. The brace 10 is first positioned such that the first brace portion 14 is located on a first portion of the patient's limb 12 on a first side of the joint and the second brace portion 16 is connected on a second portion of the patient's limb 12 on the second side of the joint. The straps 20 (shown in phantom lines in FIG. 1) are adjusted to secure the brace 10 to the patient's limb 12.

The first lock element 156 on the tension module 100 is then released such that the slider 102 can be moved within the housing 104 against the resilient force of the springs 108. The tension module 100 may be removably connected to the brace 10 with the VELCRO™ or another similar type of releasable fastener, as shown, or may be remotely located to another position by the patient.

The control knob 138 is turned by the patient in one of a clockwise or counter clockwise direction, depending on whether a clockwise or counter-clockwise moment is to be applied to the patient's arm for stretching contracted tissue, until the stiffness of the contracted joint prevents further movement of the first brace portion 14 relative to the second brace portion 16. At this point, as the patient continues to turn the control knob 138 and the one of the movable inner cables 122a, 124a continues to be wound onto the shaft 110, the slider 102 moves in the housing 104 against the resilient force of the springs 108, since the immobility of the patient's joint prevents further relative movement between the first and second brace portions 14, 16. The control knob 138 is turned until the indicator 148 reaches a desired setting. The dynamic force of the springs 108 acting on the slider 102 is transferred through the one of the movable inner cables 122a, 124a to the second part 34 of the first drive unit 30 to apply a continuous dynamic force on the patient's joint by the resilient force creating a moment on the first brace portion 14 relative to the second brace portion 16. The resilient spring force acts against the contracted tissue to provide stretching over a long period of time.

Preferably, the brace is worn for intervals of several hours, such as when the patient is asleep in order to stretch the contracted tissue over a long period of time. Therapy can consist of gradually increasing the force applied, as indicated by the indicator dial 148.

The use of the worm 134 and gear 132 provide a self-locking adjustment to prevent the tension force on the one of the movable inner cables 122a, 124a which is being wound onto the shaft 110 from causing the shaft 110 to unwind due to the tension force.

For static tension therapy, the brace 10 is adjusted such that it can be positioned and strapped on the user's limb 12 in the same manner as noted above. The locking element 156 on the tension module 100 is left in the locked position to prevent the slider 102 from moving within the housing 104 and the slider 72 of the locking mechanism on the first drive unit 30 also remains unlocked. The patient or a therapist then turns the control knob 138 in one of a clockwise or counter-clockwise direction to rotate the shaft 110. As the shaft rotates, one of the movable inner cables 122a, 124a is wound onto to the shaft and the other is unwound from the shaft 110, depending upon the direction of rotation. The force applied to one of the movable inner cables 122a, 124a being wound onto the shaft 110 is translated to the drive unit 30, causing the two-sheave pulley 44 to rotate relative to the housing 36 in a clockwise or a counter-clockwise direction depending on the direction that the control knob 138 is turned. This causes clockwise or counterclockwise movement of the first brace portion 14 relative to the second brace portion 16 which moves the limb 12 undergoing therapy.

Because the slider 102 is locked in position, all of movement of the first and second brace portions 14, 16 is translated to the patient's limb.

Referring now to FIG. 20, the second embodiment is operated in the same manner as the first embodiment except that the dynamic tension force is created by either the first and third movable inner cables 122a, 222a or the second and fourth movable inner cables 124a, 224a being wound upon the shaft 110, depending upon the direction in which the control knob 138 is rotated to impart either a clockwise or a counter-clockwise moment through the first and second drive units 30, 230 between the first and second brace portions 14, 16 to stretch contracted tissue in the jointed limb of a patient.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A brace for applying a dynamic force to jointed limb of a patient comprising:

a first brace portion adapted for connection to a first portion of a patient's limb on a first side of a joint in the limb;

a second brace portion adapted for connection to a second portion of the patient's limb on a second side of the joint;

a pivotal connection between the first and second brace portions adapted to be generally aligned with the joint in the limb when the brace is attached to the patient's limb;

a drive unit connected to the first and second brace portions for imparting a moment on one of the first and second brace portions relative to the other of the first and second brace portions; and a tension module responsive to relative motions between the first and second brace portions and being connected to the drive unit only by at least one force transmitting flexible cable assembly which can transmit force in a flexed position, the tension module imparting a dynamic, moment generating force on the drive unit when the first and second brace portions are substantially stationary with respect to each other, and the tension module being remotely lockable from the drive unit by the at least one force transmitting flexible cable assembly.

2. A brace for applying a dynamic force to a jointed limb of a patient comprising:

a first brace portion adapted for connection to a first portion of a patient's limb on a first side of a joint in the limb;

a second brace portion adapted for connection to a second portion of the patient's limb on a second side of the joint;

a pivotal connection between the first and second brace portions adapted to be generally aligned with the joint in the limb when the brace is attached to the patient's limb;

a tension module including;

a slider mounted for sliding movement against a resilient force, at least one resilient element in contact with the slider for generating the resilient force, and a rotatable shaft mounted on the slider;

first and second cable assemblies, each having a movable inner cable having first and second ends, the first ends of the first and second movable inner cables being wound on the shaft, with the first movable inner cable of the first cable assembly being wound in a clockwise direction on the shaft and the second movable inner cable of the second cable assembly being wound in a counter-clockwise direction on the shaft; and a first drive unit having a first part attached to one of the first and second brace portions, and a second part, which is movable with respect to the first part, attached to the other of the first and second brace portions, the second ends of the movable inner cables being attached to the second part such that rotation of the rotatable shaft in a clockwise direction applies a dynamic tension force on one of the inner cables by moving the slider against the resilient force, the dynamic tension force on the one of the inner cables being transferred to the second part of the first drive unit to impart one of a clockwise moment and a counter clockwise moment on the first brace portion relative to the second brace portion, and rotation of the rotatable shaft in a counter-clockwise direction applies a dynamic tension force on the other of the inner cables, the dynamic tension force on the other of the inner cables being transferred to the second part of the first drive unit to impart the other of the clockwise moment and the counter-clockwise moment on the first brace portion relative to the second brace portion.

3. The brace of claim 2 wherein the tension module includes a housing in which the slider is movably positioned and the cable assemblies further comprise an outer sheath, the inner cable being slidably disposed within the outer sheath, the outer sheaths of the cable assemblies have first and second ends, the first ends of the outer sheaths being affixed to the housing and the second ends of the outer sheaths being affixed to the first part of the first drive unit.

4. The brace of claim 2 wherein the second part of the first drive unit comprises a two sheave pulley pivotally attached to the first part, the first movable inner cable being wound in one of a clockwise and a counter-clockwise direction on one of the two sheaves, and the second movable inner cable being wound in the other of the clockwise and counter-clockwise directions on the other of the two sheaves.

5. The brace of claim 2 wherein the tension module is removably attached to one of the first and second brace portions.

6. The brace of claim 2 wherein the first and second cable assemblies are of a sufficient length such that the tension module can be located remotely from the brace.

7. The brace of claim 2 further comprising a second drive unit located on the opposite side of the joint from the first drive unit, the second drive unit having first and second parts, with the first part of the second drive unit being connected to the first brace portion, and the second part of the second drive unit being connected to the second brace portion;

third and fourth cable assemblies being connected between the tension module and the second drive unit, the third and fourth cable assemblies each having an outer sheath and a movable inner cable having first and second ends, each movable inner cable being slidably disposed within the outer sheath, the first ends of the third and fourth movable inner cables being wound on the shaft, with the third movable inner cable of the third push-pull cable assembly being wound in a clockwise direction on the shaft and the fourth movable inner cable of the fourth push-pull cable assembly being wound in a counter-clockwise direction on the shaft; and the second ends of the third and fourth movable inner cables being attached to the second part of the second drive unit such that rotation of the rotatable shaft in a clockwise direction applies a dynamic tension force on one of the third and fourth inner cables by moving the slider against the resilient force, the dynamic tension force on the one of the third and fourth inner cables being transferred to the second part of the second drive unit to impart one of a clockwise moment and a counter-clockwise moment on the first brace portion relative to the second brace portion, and rotation of the rotatable shaft in a counter-clockwise direction applies a dynamic tension force on the other of the third and fourth inner cables, the dynamic tension force on the other of the third and fourth inner cables being transferred to the second part of the second drive unit to impart the other of the clockwise moment and the counter-clockwise moment on the first brace portion relative to the second brace portion.

8. The brace of claim 7 wherein the second part of the second drive unit comprises a two sheave pulley rotatably attached to the first part of the second drive unit, the second end of the third movable inner cable being wound in one of a clockwise and a counter-clockwise direction on one of the two sheaves, and the second end of the fourth movable inner cable being wound in the other of the clockwise and counter-clockwise directions on the other of the two sheaves.

9. The brace of claim 2 wherein a gear is located on the rotatable shaft, and a worm mounted on the slider is drivingly engaged with the gear, the worm being actuatable by a control knob.

10. The brace of claim 9 wherein the tension module includes a housing in which the slider is movably positioned, and the control knob extends through a slot in the housing, the slot extending parallel to a direction of travel of the slider to allow the control knob to move with the slider.

11. The brace of claim 10 further comprising a row of teeth located along the slot, and an indicator rotatably mounted to the slider which extends through the slot and engages the teeth such that movement of the slider causes the indicator to change.

12. The brace of claim 11 wherein the indicator is a dial affixed to a gear which engages the teeth located along the slot such that movement of the slider causes the dial to rotate.

13. The brace of claim 2 further comprising a first lock element located on the tension module for fixing the position of the slider to prevent movement relative to the tension module.

14. The brace of claim 2 further comprising a second lock element located on the drive unit for fixing the position of the first part relative to the second part.

15. The brace of claim 2 wherein the first and second brace portions comprise frame members adapted to be adjustable positioned on the upper and lower portions of a patient's arm, and the pivotal connection is aligned with a patient's elbow.

16. A method of applying a dynamic force to a patient's limb to stretch contracted tissue, comprising the steps of:

(a) positioning a brace having a first brace portion pivotally connected to a second brace portion such that the first brace portion is adapted for connection to a first portion of a patient's limb on a first side of a joint in the limb and the second brace portion is adapted for connection to a second portion of the patient's limb on a second side of the joint;

(b) rotating a shaft in one of a clockwise and a counter-clockwise direction, the shaft being connected to a slider mounted in a tension module for movement against a resilient force, the rotation of the shaft creating a dynamic tension force in one of a first movable inner cable and a second movable inner cable wound around the shaft, the first movable inner cable being wound in a clockwise direction around the shaft and the second movable inner cable being wound in a counter-clockwise direction around the shaft, rotation of the shaft causing one of the first and second movable inner cables to wind up on the shaft moving the slider against the resilient force; and (c) applying a moment in one of a clockwise and a counter-clockwise direction on the first brace portion relative to the second brace portion via the one of the first and second movable inner cables which is being wound upon the shaft acting on a drive unit, the drive unit having a first part fixed to the first brace portion and a second part fixed to the second brace portion, the first and second movable inner cables being attached to the second part such that the tension force on the one of the first and second inner cables resulting from rotation of the shaft is transferred to the second part of the first drive unit to impart one of a clockwise and a counter-clockwise moment on the first brace portion relative to the second brace portion to apply a dynamic load to the patient's limb to stretch the contracted tissue.

\* \* \* \* \*